(12) United States Patent  
Dubielczyk

(10) Patent No.: US 11,147,456 B2  
(45) Date of Patent: *Oct. 19, 2021

(54) MARKER WITH LIGHT EMITTING AREA FOR USE IN DETERMINING VITAL SIGN INFORMATION

(71) Applicant: KONINKLIJKE PHILIPS N. V., Eindhoven (NL)

(72) Inventor: Alexander Dubielczyk, Gaertringen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1122 days.

This patent is subject to a terminal disclaimer.

(21) Appl. No.: 14/174,875

(22) Filed: Feb. 7, 2014

(65) Prior Publication Data

US 2014/0243648 A1 Aug. 28, 2014

Related U.S. Application Data

(60) Provisional application No. 61/767,862, filed on Feb. 22, 2013.

(30) Foreign Application Priority Data

Feb. 22, 2013 (EP) ..................... 13156366

(51) Int. Cl.
*A61B 5/00* (2006.01)
*A61B 5/1455* (2006.01)
*A61B 5/024* (2006.01)

(52) U.S. Cl.
CPC .......... *A61B 5/0059* (2013.01); *A61B 5/0071* (2013.01); *A61B 5/02416* (2013.01);

(Continued)

(58) Field of Classification Search
None
See application file for complete search history.

(56) References Cited

U.S. PATENT DOCUMENTS 6,352,517 B1 3/2002 Flock et al.
6,631,286 B2 * 10/2003 Pfeiffer ................ A61B 5/0059
348/E5.029

(Continued)

FOREIGN PATENT DOCUMENTS

AU 2012203576 A1 7/2012
DE 3922365 A1 6/1990

(Continued)

OTHER PUBLICATIONS

Cala, S.J. et al., "Chest Wall and Lung Volume Estimation by Optical Reflectance Motion Analysis", 1996, J. Appl. Physiol., 81: 2680-2689, © 1996 the American Physiological Society.

(Continued)

*Primary Examiner* — Oommen Jacob
*Assistant Examiner* — Shahdeep Mohammed

(57) ABSTRACT

A system, particularly a photo-plethysmographic system, determines vital sign information of a subject. A marker includes a marker area such as fluorescent or luminescent pigments, that emits light towards a skin of the subject. Light reflected by the skin is encoded with information about blood in the skin. An attachment layer attaches the marker to the subject. A detector, such as an optical camera, detects radiation reflected from the skin of the subject, and an analysis processor determines the vital sign information, such as heart rate and blood oxygen ($SpO_2$), of the subject from the detected radiation reflected from the skin of the subject.

19 Claims, 5 Drawing Sheets

(52) U.S. Cl.
CPC ........ *A61B 5/14556* (2013.01); *A61B 5/6814* (2013.01); *A61B 5/6824* (2013.01); *A61B 5/6833* (2013.01); *A61B 2562/0233* (2013.01); *A61B 2562/164* (2013.01)

(56) References Cited

U.S. PATENT DOCUMENTS

| | | | |
|---|---|---|---|
| 2007/0100219 A1* | 5/2007 | Sweitzer | A61B 5/0002 |
| | | | 600/323 |
| 2007/0142715 A1 | 6/2007 | Banet et al. | |
| 2008/0149701 A1 | 6/2008 | Lane | |
| 2009/0146080 A1* | 6/2009 | Liebsch | G01N 21/6408 |
| | | | 250/484.4 |
| 2009/0156988 A1 | 6/2009 | Ferren et al. | |
| 2009/0187086 A1* | 7/2009 | Benaron | A61B 5/0261 |
| | | | 600/323 |
| 2010/0036209 A1 | 2/2010 | Ferren et al. | |
| 2010/0185100 A1* | 7/2010 | Urban | A61B 5/0059 |
| | | | 600/475 |
| 2011/0263950 A1 | 10/2011 | Larson et al. | |
| 2011/0290005 A1* | 12/2011 | Hart et al. | 73/37.9 |
| 2012/0253201 A1 | 10/2012 | Reinhold | |
| 2013/0131471 A1* | 5/2013 | Locke | A61B 5/0071 |
| | | | 600/317 |
| 2013/0267854 A1* | 10/2013 | Johnson | A61B 5/0082 |
| | | | 600/473 |
| 2014/0046191 A1* | 2/2014 | Anker | A61B 5/1127 |
| | | | 600/473 |

FOREIGN PATENT DOCUMENTS

| | | |
|---|---|---|
| JP | 2009025290 | 2/2009 |
| WO | 9628086 A1 | 9/1996 |
| WO | 2011076886 A2 | 6/2011 |
| WO | WO 2011/112559 A2 * | 9/2011 |
| WO | 2012093311 A1 | 7/2012 |

OTHER PUBLICATIONS

Verkruysse, W., et al., "Remote Plethysmographic Imaging Using Ambient Light", 2008, Optics Express; 16(26) 21434-21445.
Wieringa, F.P., et al., "Contactless Multiple Wavelength Photoplethysmographic Imaging: A First Step Toward SpO2 'Camera Technology'", 2005; Annals of Biomedical Engineering; 33(8) 1034-1041.

* cited by examiner

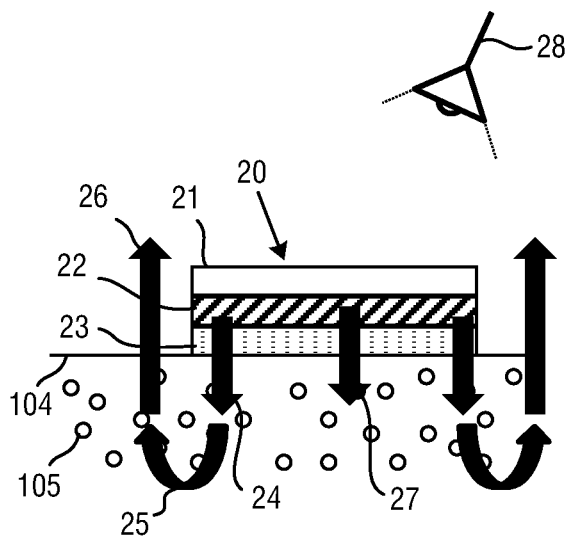
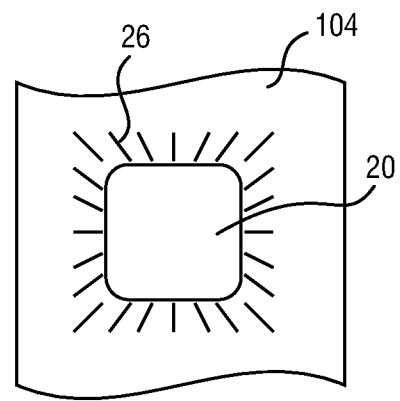
FIG.2A  FIG.2B
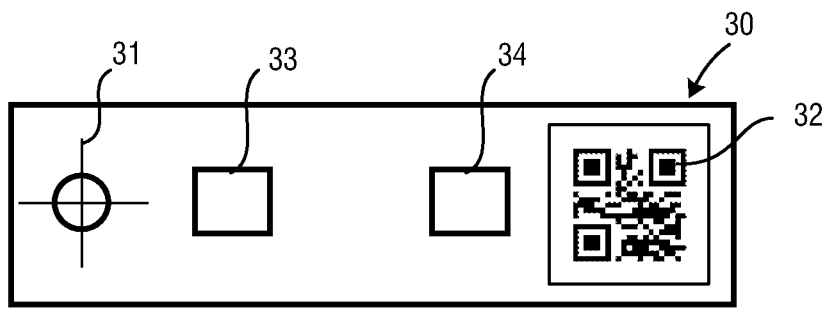
FIG.3A
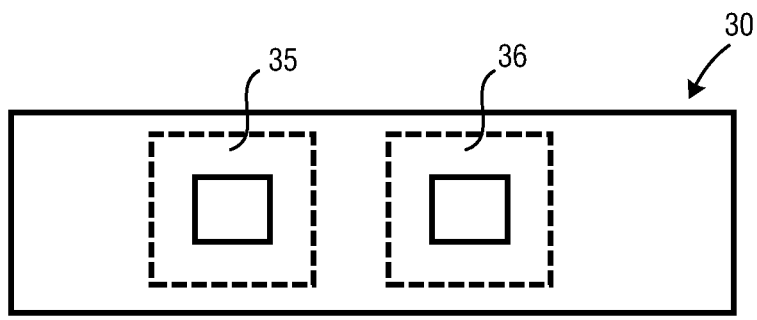
FIG.3B

MARKER WITH LIGHT EMITTING AREA FOR USE IN DETERMINING VITAL SIGN INFORMATION

CROSS REFERENCE TO RELATED APPLICATIONS

This application claims the benefit of U.S. provisional application Ser. No. 61/767,862 filed Feb. 22, 2013 and European provisional application serial no. 13156366.0 filed Feb. 22, 2013, both of which are incorporated herein by reference.

FIELD OF THE INVENTION

The present invention relates to a marker for use in determining vital sign information of a subject. Further, the present invention relates to optical measurement approaches which can be used for remotely determining vital signs of an observed subject. In this context, optical measurement may refer to photo-plethysmography (PPG) and, more specifically, to pulse oximetry.

BACKGROUND OF THE INVENTION

Vital signs of a person, for example the heart rate (HR), the respiration rate (RR) or the blood oxygen saturation, serve as indicators of the current state of a person and as powerful predictors of serious medical events. For this reason, vital signs are extensively monitored in inpatient and outpatient care settings, at home or in further health, leisure and fitness settings.

One way of measuring vital signs is plethysmography. Plethysmography generally refers to the measurement of volume changes of an organ or a body part and in particular to the detection of volume changes due to a cardio-vascular pulse wave traveling through the body of a subject with every heart beat.

Photoplethysmography (PPG) is an optical measurement technique that evaluates a time-variant change of light reflectance or transmission of an area or volume of interest. PPG is based on the principle that blood absorbs light more than surrounding tissue, so variations in blood volume with every heart beat affect transmission or reflectance correspondingly. Besides information about the heart rate, a PPG waveform can comprise information attributable to further physiological phenomena such as the respiration. By evaluating the transmissivity and/or reflectivity at different wavelengths (typically red and infrared), the blood oxygen saturation can be determined.

Conventional pulse oximeters for measuring the heart rate and the oxygen saturation of a subject are attached to the skin of the subject, for instance to a finger tip, earlobe or forehead. Therefore, they are referred to as 'contact' PPG devices. A typical pulse oximeter comprises a red LED and an infrared LED as light sources and one photodiode for detecting light that has been transmitted through patient tissue. Commercially available pulse oximeters quickly switch between measurements at a red and an infrared wavelength and thereby measure the transmissivity of the same area or volume of tissue at two different wavelengths. This is referred to as time-division-multiplexing. The transmissivity over time at each wavelength gives the PPG waveforms for red and infrared wavelengths. Although contact PPG is regarded as a basically non-invasive technique, contact PPG measurement is often experienced as being unpleasant, since the pulse oximeter is directly attached to the subject and any cables limit the freedom to move.

Recently, non-contact, remote PPG devices for unobtrusive measurements have been introduced. Remote PPG utilizes light sources or, in general radiation sources, disposed remotely from the subject of interest. Similarly, also a detector, e.g., a camera or a photo detector, can be disposed remotely from the subject of interest. Therefore, remote photoplethysmographic systems and devices are considered unobtrusive and well suited for medical as well as non-medical everyday applications.

Verkruysse et al., "*Remote plethysmographic imaging using ambient light*", Optics Express, 16(26), 22 Dec. 2008, pp. 21434-21445 demonstrates that photoplethysmographic signals can be measured remotely using ambient light and a conventional consumer level video camera.

Camera based, contactless physiological measurements require enough light of appropriate wavelengths to extract the desired vital sign information. This can be achieved by ensuring, that the ambient illumination is set up accordingly. During sleep time, however, it can be a big discomfort for patients or other monitored subjects, if the light has to be turned on during a measurement. Furthermore, it is important that the optical spectrum of the illumination meets the requirements. For example, it is important for measuring the oxygen saturation of blood to have light of defined wavelengths, typically red and infrared.

SUMMARY OF THE INVENTION

It is an object of the present invention to enable contactless vital sign measurements in dark rooms, for example at night, or in cases where the optical spectrum of the ambient illumination does not contain the wavelengths that are required for a certain measurement.

In a first aspect of the present invention a marker for use in determining vital sign information of a subject is presented that comprises a marker area that emits light towards a skin of the subject for determining vital sign information from the reflected light, and an attachment element that attaches the marker to the subject.

In a further aspect of the present invention a system for determining vital sign information of a subject is presented that comprises the marker as described above, a detection unit that detects radiation emitted by the marker towards a skin of the subject and reflected from the skin of the subject, and an analysis unit that determines the vital sign information of the subject from the detected radiation reflected from the skin of the subject.

In a further aspect of the present invention a device for use with the marker as described above is presented that comprises a detection unit that detects radiation emitted by the marker towards a skin of the subject and reflected from the skin of the subject, and an analysis unit that determines the vital sign information of the subject from the detected radiation reflected from the skin of the subject.

In a further aspect of the present invention a method for determining vital sign information of a subject is presented that comprises the steps of applying the marker as described above to the subject, detecting radiation emitted by the marker towards a skin of the subject and reflected from the skin of the subject, and determining the vital sign information of the subject from the detected radiation reflected from the skin of the subject.

In a further aspect of the present invention a computer program is presented that comprises program code means for, when carried out on a computer, causing the computer to carry out the steps of detecting radiation emitted by a marker, applied to a subject, towards a skin of the subject and reflected from the skin of the subject, and determining the vital sign information of the subject from the detected radiation reflected from the skin of the subject.

Preferred embodiments of the invention are defined in the dependent claims. It shall be understood that the claimed system, device, method and computer program have similar and/or identical preferred embodiments as the claimed marker and as defined in the dependent claims.

The inventors have found that it is advantageous to selectively illuminate a region of interest of a skin of a subject for whom vital sign information is to be determined. In particular during the night this enables unobtrusive vital sign measurements. Instead of broadly illuminating an entire scenery, it is sufficient to only illuminate the region of interest. According to the invention, this is achieved by a marker comprising a marker area for emitting light towards a skin of the subject. The marker further comprises an attachment element that attaches the marker to the subject. Hence, the marker is directly applied to the region of interest and emits light towards the skin of the subject directly where it is needed. The light emitting marker can be applied to clothing, a blanket, bed sheet or any item in proximity to the subject. Advantageously, the marker is directly applied to the skin of the skin of the subject. Since the light emitting marker is directly applied to the skin of the subject, the correct region of interest of the skin tissue is illuminated also if the patient moves.

The marker emits light towards the skin of the subject. Some of the light penetrates the skin of the subject, in particular the upper layers of the skin tissue, and is reflected from inside the tissue. The reflected light has a time-variant intensity due to the time-variant absorption and/or transmission of light within the tissue. This time-variant intensity is analyzed to the determine the vital sign information of the observed subject. The absorption and/or transmission varies because of volume changes of blood vessels due to the cardio-vascular pulse wave traveling through the body of a subject with every heart beat.

The interaction of light with biological tissue is complex and includes the optical processes of (multiple) scattering, backscattering, absorption, transmission and (diffuse) reflection. The term "reflect" as used in this context is not to be construed as limited to specular reflection but comprises the afore-mentioned types of interaction of light with tissue and any combinations thereof.

The term 'vital sign' as used in the context of the present invention refers to a physiological parameter of a subject and derivative parameters. In particular, the term "vital sign" comprises heart rate (HR) (sometimes also called pulse rate), heart rate variability (pulse rate variability), pulsatility strength, perfusion, perfusion indicator, perfusion variability, Traube Hering Mayer waves, respiratory rate (RR), body temperature, blood pressure, a concentration of a substance in blood and/or tissue, such as an oxygen saturation or a glucose level.

The term 'vital sign information' as used in the context of the present invention comprises the one or more measured vital signs as defined above. Furthermore, the term 'vital sign information' comprises data referring to a physiological parameter, corresponding waveform traces or data referring to a physiological parameter of a time that can serve for subsequent analysis.

The term 'area' as used in the context of the present invention also comprises a plurality of sub-areas that are not necessarily connected to each other.

According to a preferred embodiment, the marker area comprises at least one of fluorescent pigments and luminescent pigments that emit light towards the skin of the subject. Advantageously, the marker area that emits light towards a skin of the subject comprises a substance that illuminates the measurement site by luminescence, thus in particular by chemiluminescence due to a chemical reaction or alternatively by phosphorescence.

Alternatively, the marker area that emits light towards a skin of the subject comprises a substance that converts wavelengths from incident ambient light to a different wavelength by fluorescence. Fluorescent pigments convert light at a first wavelength to light at a second wavelength. Advantageously, said first wavelength is a non-visible wavelength. Using fluorescence, it is possible to illuminate the measurement site with non-visible ambient light, for example ultra-violet or infrared light without disturbing the patient during the night. Optionally fluorescent and luminescent pigments are combined in the same marker in the same or separate marker areas.

The conversion of wavelengths by fluorescence also helps in vital sign measurements during the daytime when the ambient light spectrum does not contain wavelengths that are required for the measurement. For example, normal gas-discharge lamps often do not contain enough infrared light to do a measurement of blood oxygen saturation. Fluorescent pigments can convert energy from arbitrary available wavelengths to the specific wavelengths needed for the measurement.

As used herein, the term "wavelength" also refers to a band of wavelengths or a wavelength portion. It is to be understood as a spectral range having a limited spectral width. For example, for an optical filter the term "wavelength" refers to a passband of the filter. Hence, the term "wavelength" is not limited to a single wavelength but is also used for a wavelength range, for example of some nanometers or some tens of nanometers, around a center wavelength. Moreover, the term "wavelength" in the context of filter can also refer to multiple discontinuous spectral ranges of one and the same filter element.

According to a further embodiment of the present invention, the marker comprises at least one of a first marker area that emits light at a first wavelength and a second marker area that emits light at a second wavelength. The first marker area and the second marker area can be separate, directly adjacent, overlapping or can also coincide. The use of at least partially separate first marker area and second marker area is advantageous since the first marker and the second marker area thereby define spatially separate areas that can be evaluated for determining vital sign information. Each marker area is configured to emit light at a different wavelength so that the concentration of a substance can be determined based on a comparison of the light reflected from the tissue at the two different wavelengths. The use of this kind of marker has the advantage that no specific additional filtering at a detection unit such as a camera is needed. The different areas of different wavelengths can be separated in the detection unit, an image processing unit or an analysis unit by spatial decomposition. Thus, a single detection unit can acquire all the required information which is beneficial for a low system cost.

Optionally, the marker comprises further marker areas that are configured to emit light at further wavelengths. The wavelengths of interest also comprise non-visible wavelengths of electromagnetic radiation, including infrared and ultra-violet wavelengths.

In yet another embodiment, the marker further comprises a transmission area that transmits light. It is advantageous to not only detect light that is reflected from the tissue externally surrounding the marker but also from regions that are enclosed by the marker. A transmission area can be an opening in the marker. Alternatively, a transmission area is a marker area for transmitting light at a desired wavelength or simply transparent for example over the entire visible, infrared and ultraviolet spectrum. A transmission area is also referred to as a 'window' or 'optical window'. A transmission area can optionally comprise a optical filter such as an optical filter plate that ensures that only light of the desired wavelength is transmitted. The types of filter plate include absorption filters as well as dielectric filters.

According to a variation of this embodiment, the marker comprises at least one of a first transmission area that transmits light at a first wavelength and a second transmission area that transmits light at a second wavelength. The first transmission area and the second transmission area thereby define spatially separate areas for determining the vital sign information. Each transmission area is configured to transmit light at a different wavelength, so that the concentration of the substance can be determined based on the comparison of light at the two different wavelengths with the advantages discussed above.

In a further embodiment, the marker comprises an opaque marker area. Advantageously, an opaque marker area ensures that light from the marker area for emitting light towards a skin of the subject is only or at least predominantly emitted towards a skin of the subject. The opaque marker area can be understood as a light shield on top of the light emitting marker area or a portion of the marker that at least blocks light at the wavelength or the wavelengths emitted by the light emitting marker area or areas. Light directly coming from the light emitting marker area can be much stronger than the light reflected from the skin of the subject. Thus, in the detection process, problems with a dynamic range of a detector or leakage effects from one detector pixel into its neighbors can occur, if no opaque marker area is used. Furthermore, an opaque marker area can be used to separate marker areas for emission or transmission of light at different wavelengths.

In a further embodiment, the marker comprises a reference area of predefined reflection characteristic. This reference area can be used for calibration since the reflection characteristic for a predetermined range of wavelengths is known. In particular when an optional light source that illuminates the marker and an optional control unit that controls said light source are used, the reference area can serve for adjusting a sensitivity of a detector and/or for adjusting a power and/or spectrum of a light source. The marker can also comprise more than one reference area, wherein each reference area has a different reflection characteristic. For example, a red reference area is used to determine the optical power in the red spectral region, whereas a reference area that reflects light in the infrared is used to determine the optical power in the infrared spectral region. Based on these measurements, the sensitivity of the detection unit can be adjusted. Alternatively, the measurement time is adjusted to achieve a sufficiently good signal-to-noise ratio.

Moreover, the reference area can be used to determine any temporal or spectral disturbances of the ambient light and/or an artificial light source, for example, slow changes during the day or systematic influences such as 50/60 Hertz flicker or a pulse-width modulation of the light source. The measured intensity from the first and/or second marker area can be corrected for such disturbances.

In yet another embodiment, the marker further comprises a graphical pattern. Preferably, the graphical pattern has a high image contrast, for example, a black and white pattern. Alternatively, the graphical pattern comprises different colors that can be clearly distinguished. Favorably, the graphical pattern is optimized to be machine-readable such as a barcode, a matrix barcode, alphanumerical characters, a QR-code or the like. For detection by image processing methods, it is easier to detect a specific graphical pattern in an observed scene than analyzing unspecified image features. Optionally, the graphical pattern is a machine-readable code that stores information, such as a patient identifier for assigning the measured vital sign information to a patient or a body part of the patient. The encoded information can further comprise configuration data for configuring a system for determining vital sign information for example, a required sensitivity or information about the vital sign information to be measured. Alternatively, the graphical pattern provides information about the location of a region of interest for determining vital sign information, for example a location relative to the location of the marker. The arrangement of the marker area as well as the size and/or shape of the marker can also be seen as a graphical pattern. Furthermore, a graphical pattern can be made fluorescent or luminescent as well, to make it readable in a dark environment.

In a further embodiment of the marker according to the present invention, the emission of light is activated by chemical reaction. The emission of light by luminescence due to a chemical reaction is also referred to as chemiluminescence. This can be for example achieved by lamination. In this example the marker comprises separate parts or layers that are produced and diverted independently and then attached or glued to each other right before use. Each of the separate parts comprises one of the substances that then react with each other to emit light by luminescence. As soon as the substances get in touch physically, the reaction starts.

In a further example, at least one of the substances is a component of an ink that is printed on the marker as soon as the light emission from the marker is needed. The marker comprises a carrier material that contains the second component needed for the luminescence reaction. The printing approach also works for two different inks containing each of the substances for the chemical reaction which are then mixed in the printing process.

In a further example, the marker is a first basic component while the second component is comprised in a fluid. The reaction starts as soon as the fluid is brought to the surface of the marker, for example by spraying or brushing the fluid onto it.

In a preferred embodiment of the invention, the marker comprises a carrier layer that provides mechanical stability of the marker, a light emission layer comprising at least one of fluorescent and luminescent pigments that emit light towards the skin of the subject and an attachment layer comprising an adhesive that attaches the marker to the subject. In general, the carrier layer can be thought of as an element that provides mechanical stability of the marker. For example, the carrier element can be made from a material of a group of materials comprising paper, textile, rubber or further materials, in particular materials used for patches in medical applications. Advantageously, the adhesive is a bio-compatible adhesive in particular for medical applications.

In an alternative embodiment, the light emitting marker is directly applied to the skin of the subject. For example, a type of paint, ink or dye or generally a fluid or liquid that comprises a light emitting substance is directly applied to the skin of the subject to form the marker area for emitting light towards the skin of the subject, such that no further mechanical stabilization is needed. The skin of the subject provides the required mechanical stabilization. In this context, attachment element refers to the carrier fluid that comprises the light emitting substance.

In an aspect of the present invention, an applicator that applies the marker as described above to a skin of a subject is presented. The applicator is used to apply the light emitting marker directly to the skin of the subject. For example, the applicator is a type of pen or highlighter that comprises the carrier fluid and the light emitting substance. Alternatively, the applicator is a stamp for stamping or rubber printing the substance for the marker area for emitting light towards the skin of the subject directly on the skin of the subject. Optionally, light emission is activated by a chemical reaction when the marker is applied to the skin of the subject. Alternatively, two inks with components for a luminescent reaction are brought into contact on the skin of the subject by rubber printing them on top of each other.

The context of the present invention is a system for determining vital sign information of a subject comprising a marker as described above, a detection unit and an analysis unit.

As used herein, the term "detection unit" refers to a device for detecting electromagnetic radiation. It is configured to detect radiation emitted by the marker towards a skin of the subject and reflected from the skin of the subject. Hence, light that has penetrated into the skin tissue of the subject and is reflected therefrom can be detected. This reflected radiation comprises the vital sign information of interest. In a preferred embodiment, the detection unit is a camera with an image sensor, such as a CCD or CMOS image sensor that comprises an array of light-sensitive pixels. The output of the detection unit is referred to as radiation data. For example, the radiation data is a series of images over time, thus a video stream. The camera can be a monochrome or color camera.

The received radiation, in particular the radiation received from the surroundings of the marker area for emitting light towards a skin of the subject and also from any optional transmission area comprises light that has penetrated into the skin and is reflected from inside the tissue. This received radiation has a time-variant intensity due to the time-variant absorption and/or transmission of light within the tissue.

Optionally, the system further comprises a light source. This light source can be at a wavelength that is evaluated in determining the vital sign information of the subject and/or at a wavelength, in particular a non-visible wavelength, which is then converted to the wavelength desired for measurement by fluorescent pigments of the marker area for emitting light towards the skin of the subject. Further optionally, the system comprises a control unit to control the light power such that the detection unit can be operated in its optimum operating point in particular such that, for example, noise or saturation effects do not disturb the measurement.

The analysis unit is configured to determine the vital sign information of the subject from the detected radiation reflected from the skin of the subject. The analysis unit receives the radiation data from the detection unit. For determining the heart rate of the subject it is sufficient to evaluate the time-variant radiation received at a single wavelength. However, for determining a concentration of a substance, for example for determining a blood oxygen saturation or a glucose level, the analysis of radiation at different wavelengths is required.

In yet another embodiment, the system further comprises an image processing unit for identifying the marker in the detected radiation. The image processing unit is an optional element that is located between the detection unit and the analysis unit. The image processing unit receives radiation data, for example a video stream, from the detection unit. The image processing unit comprises image processing means for identifying the marker in the received radiation data. For example, the marker has particular features that can be identified in an image of video stream. Analysis methods known from image processing and video analysis can be applied. The image processing unit can provide the analysis unit with processed radiation data that comprises information about the location of the marker in the radiation data. In particular in darkness, the radiation caused by the light emitting marker can easily be identified. For example, the image processing unit identifies a pixel or a group of pixels that represent portions of the image sensor that received light from the marker or reflected light from the surroundings of the marker. Optionally, the image processing unit is incorporated into the analysis unit.

BRIEF DESCRIPTION OF THE DRAWINGS

These and other aspects of the invention will be apparent from and elucidated with reference to the embodiment(s) described hereinafter. In the following drawings

FIG. 2a shows a side view of a first embodiment of a marker;

FIG. 2b shows a top view of the first embodiment of the marker;

FIG. 3a shows a top view of a second embodiment of a marker;

FIG. 3b shows a bottom view of the second embodiment of the marker;

DETAILED DESCRIPTION OF THE INVENTION

Figure 1:
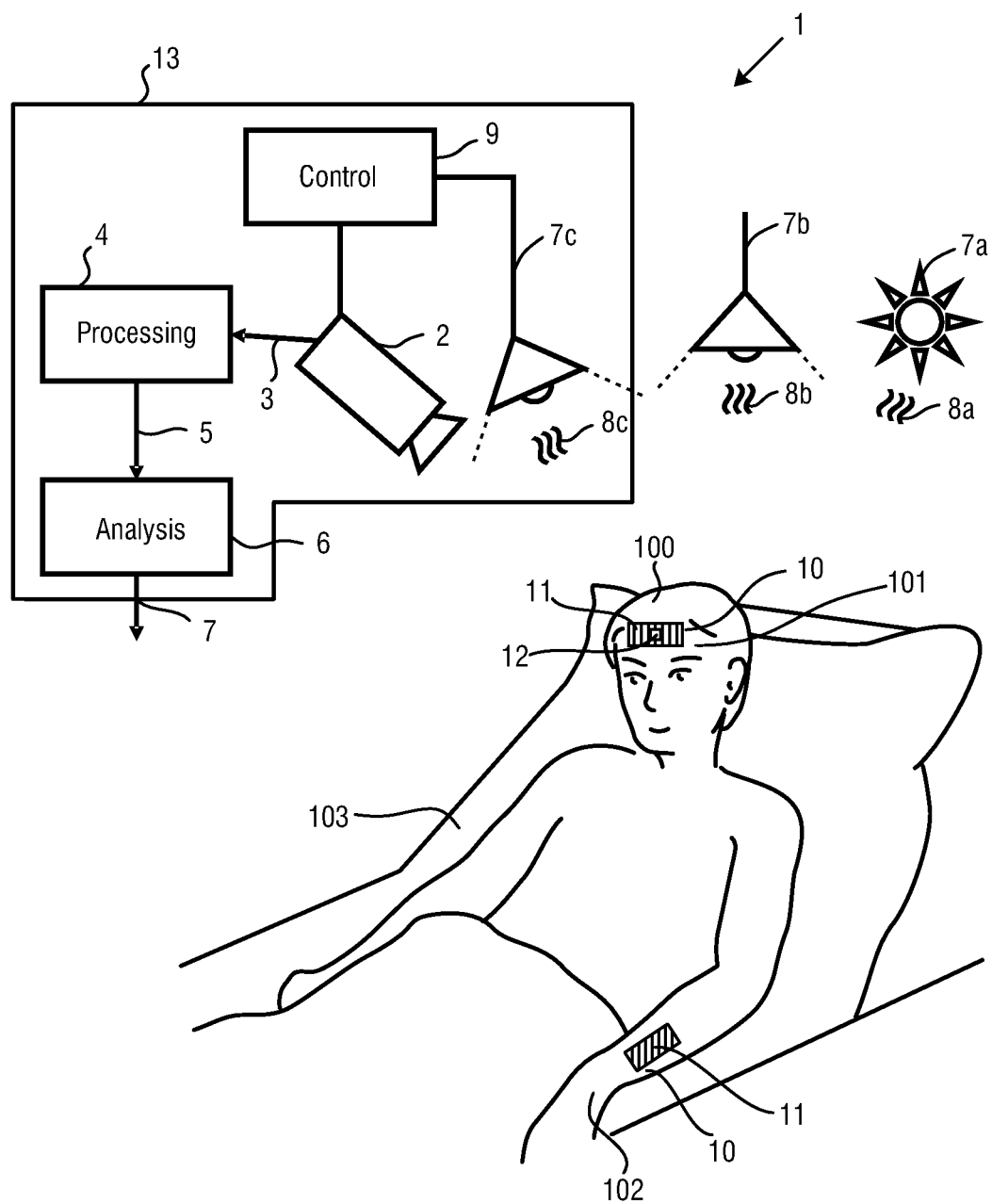
FIG. 1 shows an exemplary embodiment of a system for determining vital sign information of a subject according to the present invention.

FIG. 1 shows an exemplary embodiment of a system 1 for determining vital sign information of a subject that comprises a marker 10 and a device 13 for use with said marker. The marker 10 comprises a marker area 11 for emitting light towards a skin of the subject. The light is emitted towards the skin of the subject for determining vital sign information from the reflected light. The device 13 for use with the marker 10 comprises a detection unit 2 and an analysis unit 6 as the basic components. In this example, the system for determining vital sign information of the subject is employed in a clinical setting, where the subject 100 lies in bed 103.

The detection unit 2 is adapted to detect radiation emitted by the marker 10 towards a skin of the subject 100 and reflected from the skin of the subject 100. In other words, light is emitted by the marker 10 towards the skin of the subject, where at least a part of it is reflected. The reflected light is then detected by the detection unit 2. In this example, the detection unit 2 is connected to an optional image processing unit 4. The detection unit 2 provides radiation data 3 that represents the detected radiation to the image processing unit 4 in form of a video stream. The image processing unit 4 identifies the marker 10 in the radiation data 3. The image processing unit 4 in turn is connected to the analysis unit 6. The image processing unit 4 provides pre-processed radiation data 5 to the analysis unit 6. The pre-processed radiation data 5 in this example comprises information about which region of the images of the video stream in the radiation data 3 depict the marker 10 and the surroundings of the marker 10. The analysis unit 6 in turn determines the vital sign information 7 of the subject from a time-variant intensity from radiation received from the surroundings of the marker 10, i.e., that area of the skin where light that has been emitted by the marker towards the skin is reflected from. In this example with a single marker area, the vital sign information comprises a heart rate.

The image processing unit 4 for identifying the marker 10 can also be incorporated into the analysis unit 6. Alternatively, the radiation data 3 is directly provided to the analysis unit 6. In that case, the marker 10 can be determined by manually selecting the marker 10 and the surrounding area in the images of the video stream. Alternatively, the subject 100 with the marker 10 has to be located in a predetermined position within the field of the detection unit 2 such that the marker 10 is located at a predetermined position. However, an automated identification of the marker 10 in the radiation data 3 by the image processing unit 4 is preferred.

In the shown example, a marker 10 is directly applied to the bare skin of the forehead 101 of the subject 100. An alternative marker 10' is located at the left forearm 102 of the subject 100. The size and shape of the marker 10, 10' can be adapted depending on the anatomic location.

The marker 10 on the forehead 101 of the subject 100 further comprises a transmission area 12 for transmitting light. Thus light reflected from the tissue of the subject in the transmission area 12 can also be detected by the detection unit 2 and evaluated by the analysis unit 6.

In a system according to the prior art, the scenery has to be illuminated by a source of radiation, such as sunlight 7a or an artificial light source 7b. The radiation source 7a, 7b directly or indirectly emits radiation 8a, 8b towards the subject 100.

With the system 1 according to the present invention, no such light sources 7a, 7b are needed anymore; at least the radiation sources do not have to contain the wavelengths that are required for certain vital sign measurements. For the case that the marker 10 comprises luminescent pigments for emitting light towards the skin of the subject, no ambient light sources are needed at all. For the case that the marker 10 comprises fluorescent pigments for emitting light towards the skin of the subject 100, the requirements regarding the spectrum of the ambient light can be relaxed. It is also possible to use an optional system light source 7c that emits radiation 8c towards the subject. Advantageously, the radiation 8c emitted by the system light source illuminates the measurement site with non-visible light in the ultra-violet or infrared spectral region. Thereby, the subject 100 is not disturbed, for example, during the night. Fluorescent pigments convert energy from the absorbed light 8c to the specific wavelength needed for the vital sign measurement.

An optional control unit 9 is adapted to control the sensitivity of the detection unit 2 and/or to control the power of the optional system light source 7c. Because the dynamic range of a detector or image sensor that is used as a detection unit 2 is limited, shutters and/or electronic offsets may have to be adjusted according to the lighting situation in the observed scene. The system light source 7c can be part of a control loop for setting an optimal operating point of the image sensor and of the detection unit 2. Optimal in this context refers to an output signal without signal clipping, no saturation of individual detectors of the image sensors and a good signal-to-noise ratio at least for the detector area corresponding to the marker 10, 10' and its surrounding.

FIG. 2 illustrates a marker 20 for use in determining vital sign information of a subject 100 according to the present invention. The marker 20 comprises a carrier layer 21 for providing mechanical stability to the marker 20, a light emission layer 22 for emitting light towards the skin 104 of the subject, and an attachment layer 23 comprising an adhesive for attaching the marker 20 to the skin 104 of the subject. The skin or skin tissue 104 of the subject comprises blood vessels 105.

In a first example, the light emission layer 22 emits light 24 by luminescence from luminescent pigments comprised in the light emission layer 22. In this example, the carrier layer 21 is opaque, i.e., the carrier layer 21 does not transmit light at least in the emission spectrum of the luminescent pigments.

Light 24 is emitted from the light emission layer 22 towards the skin 104 of the subject and penetrates into the skin tissue. Some of the light is absorbed, but also some of the light is reflected 25 within the tissue 104. Blood that pulsates through the blood vessels 105 in the tissue 104 affects the transmission and reflectance of the light with every heartbeat. Therefore, the portion 26 of the reflected light that exits the tissue 104 has a time-variant intensity that represents the cardio-vascular pulse wave traveling through the body of the subject with every heartbeat. Light 27 that is absorbed underneath the marker cannot be detected.

FIG. 2b shows a top view of the marker 20 applied to the skin 104 of the subject. In this example, the portion 26 of the reflected light that exits the tissue 104 can be detected in the surrounding of the marker 20.

In a second example of FIG. 2a, the light emission layer 22 comprises fluorescent pigments for emitting light towards the skin 104 of the subject. In this example, the light source 28 emits light at a first ultra-violet, non-visible wavelength towards the subject with the marker 20. The carrier layer 21 is transparent for this first wavelength.

In a third example of FIG. 2a, the carrier layer 21 is omitted. Instead of using a separate light emission layer 22 and an attachment layer 23, these layers are replaced by an ink that is directly applied to the skin 104 of the subject 100. The ink comprises luminescent pigments for emitting light. Some of the light is emitted towards the skin of the subject. Thus the ink also serves for attaching the luminescent pigments to the skin of the subject. An attachment element in this context comprises the (chemical) components of the ink the keep the ink on the skin of the subject and thereby prevent the luminescent pigments form moving.

Optionally, an additional layer of opaque ink is applied on top of the light emitting layer of ink to block the emission of light away from to skin of the subject at least in parts of the marker area. As in the previous example, the portion 26 of the reflected light that exits the tissue 104 can be detected in the surrounding of the marker 20. Known image processing techniques can be used to identify the surrounding of the marker.

FIG. 3a shows a top view of a further embodiment of a marker according to the present invention. When applied to the skin of the subject, the depicted top surface faces towards the detection unit 2 and away from the skin of the subject. The marker 30 comprises a first graphical pattern 31 and a second graphical pattern 32. Optionally, the graphical patterns also comprise fluorescent and/or luminescent pigments. Thereby, the graphical patterns can also be detected in the darkness.

The marker 30 further comprises a first transmission area 33 and a second transmission area 34 for transmitting light.

FIG. 3b shows a bottom view of the marker of FIG. 3a, i.e., the side of the marker that faces towards the skin 104 of the subject 100. The marker 30 comprises a first marker area 35 for emitting light at a first wavelength and a second marker area 36 for emitting light at a second wavelength. When applied to the skin of the subject, light at the first wavelength is predominantly detected in the first transmission area 33 and light emitted at the second wavelength is predominantly detected in the second transmission area 34. The transmission areas 33, 34 are also referred to as windows or optical windows. In this example, the optical windows are surrounded by chemically active areas that illuminate the measurement site at the tissue below the marker 30 by luminescence when the marker 30 is applied to the skin 104 of the subject 100.

Figure 4:
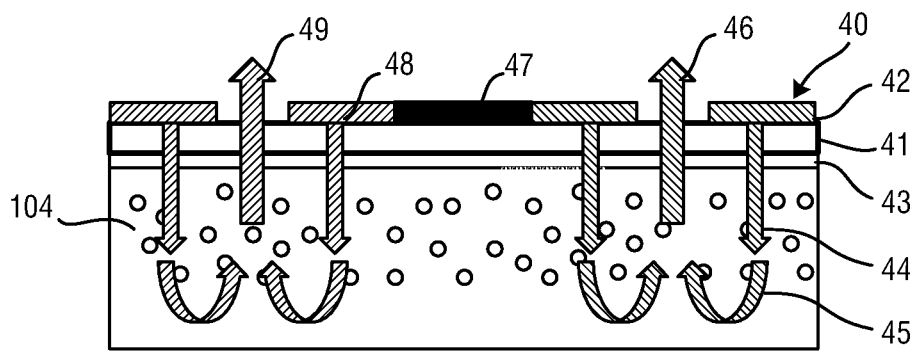
FIG. 4 shows a side view of a third embodiment of a marker.

FIG. 4 shows a similar embodiment of a marker 40 that comprises a first marker area 42 for emitting light at a first wavelength and a second marker area 48 for emitting light at a second wavelength. In this embodiment, the light emission layer comprising the first and second light emitting area 42, 48 is applied on top of a carrier layer 41 which is attached to the skin 104 of the subject by an adhesive layer 43. The carrier layer 41 in this example as well as the layer of adhesive 43 are transparent.

The first marker area 42 emits light 44 towards the skin of the subject 104. Some of the light is reflected 45 inside the tissue. Light 46 at the first wavelength exits the skin tissue 104 through the optical window formed at the center of the first marker area and light 49 at the second wavelength exits the skin tissue 104 through the optical window formed at the center of the second marker area 48. Thus, light at two different wavelengths that carries photoplethysmographic information in its time-variant intensity exits the skin of the subject at two spatially separate areas. The central portion 47 of the marker 40 is opaque and does not transmit light. This improves the separation of the two marker areas 42,48.

Figure 5:
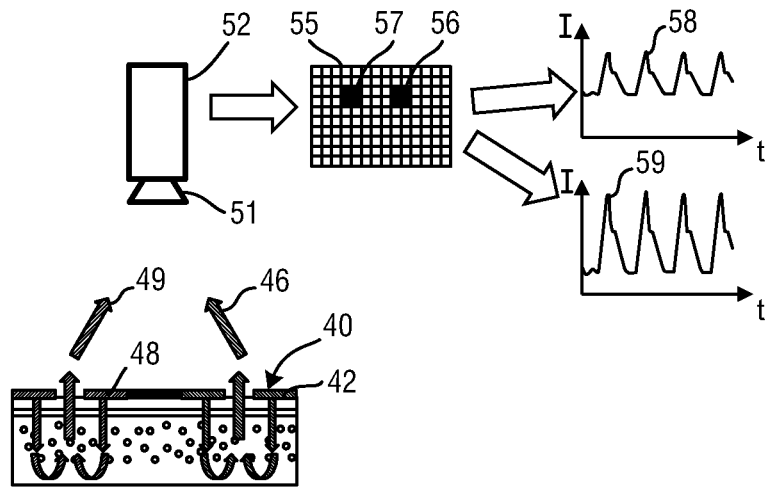
FIG. 5 shows the determination of vital sign information with the system according to the present invention.

FIG. 5 illustrates the determination of vital sign information of the subject with the system 1 according to the present invention. FIG. 5 shows a detection unit 52 and the marker 40 from FIG. 4.

The detection unit 52 comprises receiving optics 51, for example a receiver lens, and an array 55 of photodetectors or pixels that form an image sensor. Light 46 that is received from the optical window formed at the center of the first marker area 42 is imaged onto a first group or array of pixels 56. Correspondingly, light 49 received from the optical window at the center of the second marker area 48 is imaged onto a second group of pixels 57. Since the absorption of light in the tissue 104 is time-variant, the light intensity incident on the image sensor of the detection unit 22 is also time-variant. Since the absorption of light in the tissue 104 is also wavelength-dependent, the light intensity incident on the first group of pixels 56 and on the second group of pixels 57 is different. The time-variant intensity on the area of pixels 56 is depicted by a curve 58. The time-variant intensity incident on the group of pixels 57 is depicted by the curve 59.

The pulse rate of the subject can be directly determined from the time-variant intensity in one of the curves 58 or 59. However, for determining the blood oxygen saturation by photoplethysmography, at least two wavelengths are required, as exemplarily explained below.

Contact pulse oximeters typically transmit red (R) and infrared (IR) (or, more precisely, in some cases near infrared) light through a vascular tissue of the subject of interest. The respective light portions (R/IR) can be transmitted and detected in an alternating (fast-switching) manner. Given that the respective spectral portions are differently absorbed by oxygenated hemoglobin ($HbO_2$) and reduced hemoglobin (Hb), blood oxygen saturation eventually can be processed. An oxygen saturation ($SO_2$) estimation algorithm can make use of a ratio of the signals related to the red and the infrared portion. Furthermore, the algorithm can consider a non-pulsatile signal component. Typically, the PPG signal comprises a DC component and a relatively small pulsatile AC component. Furthermore, $SO_2$ estimation generally involves an empirically derived calibration factor applied to the processed values. Typically, the calibration factor (or, calibration curve) is determined upon reference measurements involving invasive blood oxygen saturation measurements. A calibration factor is required since a PPG device basically detects a ratio of (spectral) signal portions which has to be transferred into a blood oxygen saturation value which typically involves a ratio of $HbO_2$ and Hb. For instance, but not intended to limit the present disclosure, blood oxygen saturation estimation can be based on the following general equation:

$$SO_2 = \frac{HbO_2}{hbO_2 + Hb}, \quad (1)$$

whereas PPG devices merely mediately detect $HbO_2$ and Hb from the spectral response at at least two wavelengths.

Generally, the measured intensity curve 28, 29 as a characteristic signal is considered to contain a considerably constant (DC) portion and an alternating (AC) portion superimposing the DC portion. Applying signal processing measures, the AC portion can be extracted and, furthermore, compensated for disturbances. For instance, the AC portion of the characteristic signal can comprise a dominant frequency which can be highly indicative of the subject's 100 vascular activity, in particular the heart beat. Still, the characteristic signal, in particular the AC portion, can be indicative of further vital parameters. In this connection, the detection of arterial blood oxygen saturation is an important field of application. As indicated above, basically, arterial blood oxygen saturation-representative values can be computed taking into account the behavior of the AC portion of the characteristic signal at distinct spectral portions thereof.

In other words, a degree of arterial blood oxygen saturation can be reflected in different radiation absorbance at blood vessels. Furthermore, one can make use of the fact that the difference in absorbance due to the grade of oxygenation also varies significantly across different spectral portions. Moreover, also the DC portion of the signal can be utilized for blood oxygen saturation detection. Typically, the DC component represents the overall light absorption of the tissue, venous blood, and non-pulsatile arterial blood. By contrast, the AC component may represent the pulsatile arterial blood's absorption. Consequently, the determination of arterial blood oxygen saturation ($SaO_2$) can be expressed as:

$$SaO_2 = C \cdot \frac{(AC/DC)_{red}}{(AC/DC)_{infrared}}, \quad (2)$$

where C is a calibration parameter. C may stand for a large variety of calibration parameters applicable to the AC/DC relationship and should therefore not be interpreted in the strict algebraic sense of equation (2). C may, for example, represent a fixed constant value, a set of fixed constants or an adjustable calibration parameter. By way of example, another exemplary $SaO_2$ derivation model can be expressed as:

$$SaO_2 = C_1 + C_2 \cdot \frac{(AC/DC)_{red}}{(AC/DC)_{infrared}}, \quad (3)$$

where $C_1$ and $C_2$ can be considered calibration parameters of a linear approximation. In an exemplary embodiment, the signal calibration parameter determination can be directed to adjust or adapt the parameter $C_1$. Still, in the alternative, $SaO_2$ derivation may also be based on value tables deposited in (or accessible by) the analysis unit 6. The value tables (or: data bases) may provide for a discrete representation of the relationship between detected PPG signals and the desired calibration parameter. Also in that case an adaptable calibration parameter may be applied to improve the accuracy of the vital parameter determination.

It should be understood that the equations (2) and (3) are primarily presented for illustrative purposes. They should not be construed as limiting the scope of the present disclosure. In practice, the skilled person may determine and establish further appropriate $SaO_2$ derivation models. Alternative wavelength combinations, for example green and red, can be used depending on the substance to be detected. While the measurement of $SaO_2$ has been described in detail, this is to be understood as an example for the general concept of measuring the concentration of a substance in blood and/or tissue.

Figure 6:
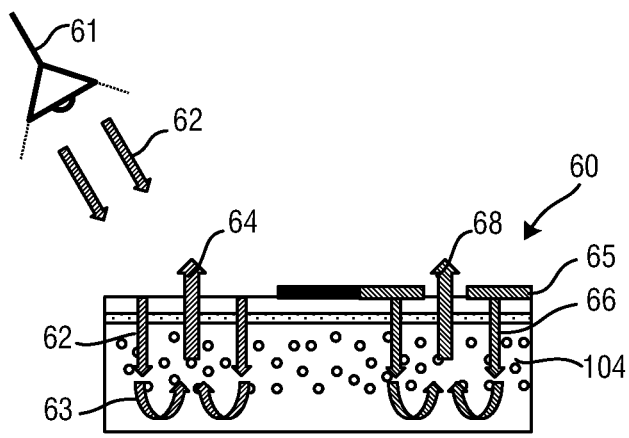
FIG. 6 shows a side view of a fourth embodiment of a marker.

FIG. 6 shows a modification of the marker 40 from FIG. 4. The second marker area is simply removed, such that the marker 60 is transparent in this area. A light source 61 emits light 62 at an infrared, non-visible wavelength onto the skin tissue 104 of the subject 100 with the marker 60. Some of the light penetrates 62 into the skin tissue, is reflected 63 and exits 64 the tissue 104 again. The light 64 that exits the tissue 104 is intensity-modulated by the pulsatile absorption variation. The first marker area 65 comprises fluorescent pigments that convert the energy from the light 62 emitted by the light source 61 to red light. Some of this red light is emitted towards the skin and penetrates 66 into the skin tissue, is reflected 67 and exits 68 the tissue 104 again. The light 68 that exits the tissue 104 at this first (red) wavelength and the light that exits the tissue 104 at the second (infrared) wavelength 64 can be used for determining the concentration of a substance in the tissue 104. Optionally, the carrier layer underneath the first marker area acts as a filter that blocks light at the wavelength of the light source 61.

Figure 7:
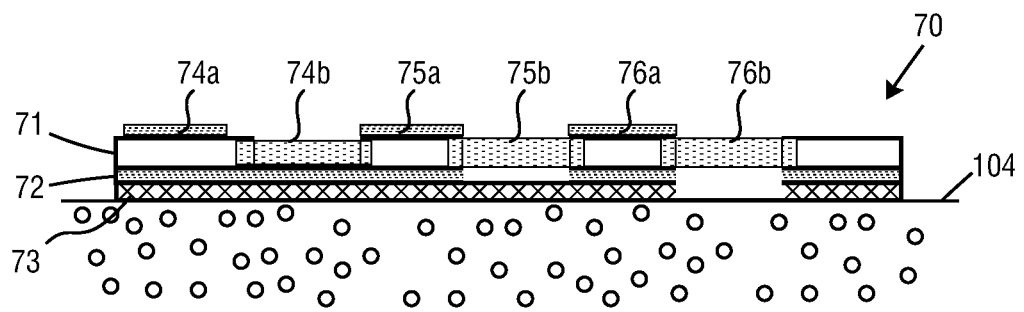
FIG. 7 shows a side view of a fifth embodiment of a marker.

FIG. 7 shows a further embodiment of a marker 70 according to the present invention. The marker again comprises a carrier layer 71, a light emission layer 72 and an attachment layer 73. The marker 70 is attached to the skin 104 of the subject 100. In this embodiment, the light emission layer 72 at least comprises luminescent pigments for emitting light at a first wavelength and luminescent pigments for emitting light at a second wavelength. Alternatively, the light emission layer 72 is a broadband emitter. The marker 70 features reference areas 74a, 75a, 76a, and transmission areas 75b, 76b configured to transmit light at two different wavelengths, and a transparent marker area 74b.

In this embodiment, the marker is a patch or band-aid that can be directly attached to the skin of the subject 100 thanks to the adhesive layer 73. Alternatively, the marker 70 itself does not comprise an adhesive but is fixed to the skin of the subject by alternative fixation means, for example by a bandage or tape that act as the attachment element of the marker.

In this embodiment, the carrier layer 71 is made from an opaque rubber-like material that does not transmit light. Therefore, the carrier element features openings or windows at the positions of the marker areas 74b, 75b, 76b. In each of the windows 74b, 75b, 76b an optical filter plate is placed wherein the optical filter plate in 75b is configured to transmit light at a first wavelength, the filter plate in 76b is configured to transmit light at a second wavelength. The optical window at 74b does not have a frequency-selective filter but is transparent so that the layer of luminescent pigments 72 can be seen by the detection unit as a reference or for calibration. Direct optical access to the light emitting layer is also advantageous to determine if the light emission still is sufficiently strong for the measurement task. Optionally, the adhesive layer 73 can be removed underneath the optical windows, as exemplary shown under 76b, for better transmission characteristics.

The reference areas 75a, 76a are reference areas for specific wavelengths. Preferentially, the color of the reference area corresponds to the transmission wavelength of the neighboring filter. For example, marker area 75b is configured to transmit green light and the reference area 75a has green color so that it can serve as a reference, in particular as to how much green light is available in the radiation that is incident on the marker. In an embodiment, where fluorescence is used, such reference areas can be used to determine if the spectrum and intensity of the ambient light is sufficient for a measurement with ambient light or if an additional system light source should be activated.

Figure 8A:
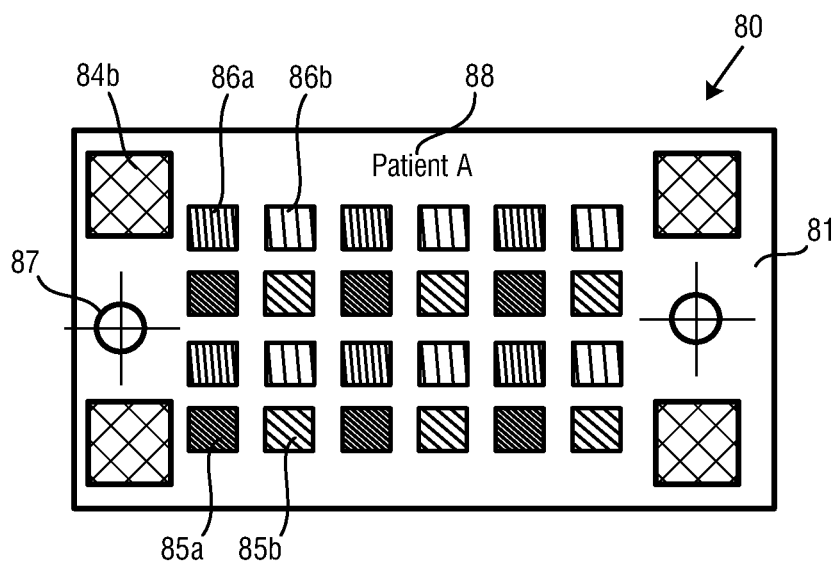
FIG. 8a shows a top view of a sixth embodiment of a marker.
Figure 8B:
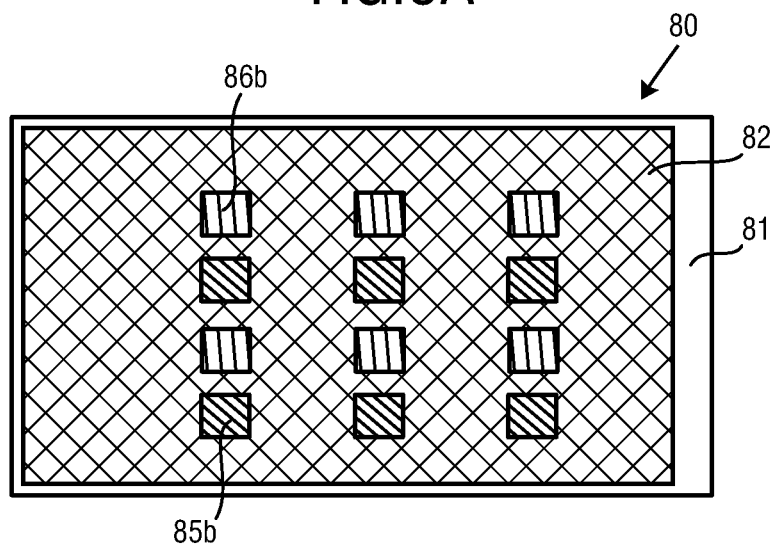
FIG. 8b shows a bottom view of the sixth embodiment of the marker.

FIG. 8a shows a top view of a further exemplary embodiment of a marker 80 according to the present invention, FIG. 8b shows a bottom view of the same. Depending on the desired measurement it can be necessary to arrange the optical windows 85b, 86b as close as possible. As shown in FIG. 7, the optical windows 85b, 86b can be combined with optical filters that prevent wavelength crosstalk between the windows. To characterize ambient light effects this can also be combined with opaque reference areas 85a, 86a of different reflectance characteristics. If filters are used in the optical windows 85b, 86b, luminescent pigments for the required wavelength can be mixed in a common light emitting layer 82 and distributed on the entire bottom surface of the marker 80.

In this embodiment, the maker comprises an opaque carrier layer 81. The light emitting layer 82 can also be seen from the top surface through transparent optical windows 84*b*.

The marker 80 further comprises graphical patterns 87 for alignment and a graphical pattern 88 in form of alphanumerical characters for patient identification.

Figure 9A:
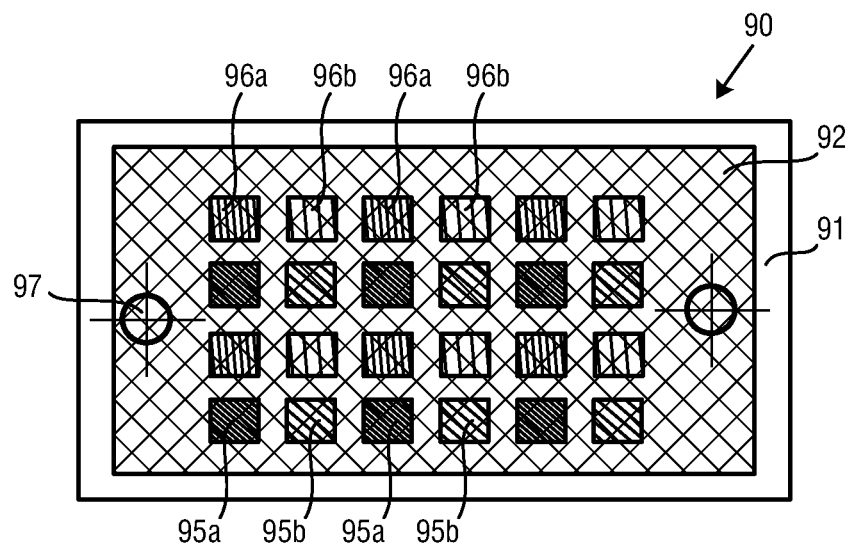
FIG. 9a shows a top view of a seventh embodiment of a marker.
Figure 9B:
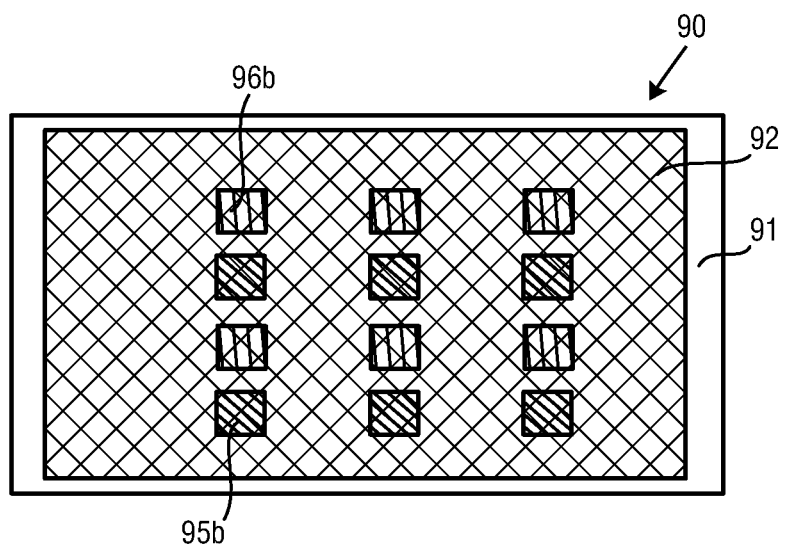
FIG. 9b shows a bottom view of the seventh embodiment of the marker.

FIG. 9*a* shows a top view of a further embodiment of a marker 90 according to the present invention, FIG. 9*b* shows a bottom view of the same. The marker 90 comprises a transparent carrier 91 and a combination of fluorescent pigments 92 that emit all needed wavelengths towards the tissue, in particular a first wavelength and a second wavelength. The marker 90 comprises reference areas 95*a* and the first wavelength and reference areas 96*a* at the second wavelength. Furthermore, the marker 90 comprises optical filters 95*b* that constitute a first transmission area for transmitting light at a first wavelength and second filters 96*b* that constitute a second transmission area for transmitting light at the second wavelength. Even though the pigments 92 emit light at the first and the second wavelength, the filters only transmit light at one desired wavelength. Thereby, signals at different wavelengths are spatially separated for spatial decomposition and subsequent analysis.

In this embodiment, the reference areas 95*a*, 96*a* and filters 95*b*, 96*b* are arranged in a check board design, however further arrangements are possible. In particular, if the signal at one wavelength is weaker than the other wavelength, a larger area can be used for the weaker wavelength to have a similar light intensity at both wavelengths. Event though the shown embodiments illustrate the use of two different wavelengths it is to be understood that additional wavelengths can be evaluated. If only a time-variant intensity is of interest, the evaluation of a single wavelength can be sufficient.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or an does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Furthermore, the different embodiments can take the form of a computer program product accessible from a computer usable or computer readable medium providing program code for use by or in connection with a computer or any device or system that executes instructions. For the purposes of this disclosure, a computer usable or computer readable medium can generally be any tangible device or apparatus that can contain, store, communicate, propagate, or transport the program for use by or in connection with the instruction execution device.

In so far as embodiments of the disclosure have been described as being implemented, at least in part, by software-controlled data processing devices, it will be appreciated that the non-transitory machine-readable medium carrying such software, such as an optical disk, a magnetic disk, semiconductor memory or the like, is also considered to represent an embodiment of the present disclosure.

The computer usable or computer readable medium can be, for example, without limitation, an electronic, magnetic, optical, electromagnetic, infrared, or semiconductor system, or a propagation medium. Non-limiting examples of a computer readable medium include a semiconductor or solid state memory, magnetic tape, a removable computer diskette, a random access memory (RAM), a read-only memory (ROM), a rigid magnetic disk, and an optical disk. Optical disks may include compact disk-read only memory (CD-ROM), compact disk-read/write (CD-R/W), and DVD.

Further, a computer usable or computer readable medium may contain or store a computer readable or usable program code such that when the computer readable or usable program code is executed on a computer, the execution of this computer readable or usable program code causes the computer to transmit another computer readable or usable program code over a communications link. This communications link may use a medium that is, for example, without limitation, physical or wireless.

A data processing system or device suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories, which provide temporary storage of at least some computer readable or computer usable program code to reduce the number of times code may be retrieved from bulk storage during execution of the code.

Input/output, or I/O devices, can be coupled to the system either directly or through intervening I/O controllers. These devices may include, for example, without limitation, keyboards, touch screen displays, and pointing devices. Different communications adapters may also be coupled to the system to enable the data processing system to become coupled to other data processing systems, remote printers, or storage devices through intervening private or public networks. Non-limiting examples are modems and network adapters and are just a few of the currently available types of communications adapters.

The description of the different illustrative embodiments has been presented for purposes of illustration and description and is not intended to be exhaustive or limited to the embodiments in the form disclosed. Many modifications and variations will be apparent to those of ordinary skill in the art. Further, different illustrative embodiments may provide different advantages as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated. Other variations to the disclosed embodiments can be understood and effected by those skilled in the art in practicing the claimed invention, from a study of the drawings, the disclosure, and the appended claims.

The invention claimed is:

1. A photo-plethysmography marker comprising:
a carrier layer;
at least one of fluorescent pigments or luminescent pigments carried by the carrier layer;
a plurality of windows defined in the carrier layer adjacent to the at least one of fluorescent pigments or luminescent pigments and configured to pass light of a first, visible wavelength and pass light of a second, invisible wavelength;
an attachment layer disposed on the carrier layer and configured to attach the carrier layer to a subject,
wherein the fluorescent pigments include a first fluorescent pigment emitting light of the first, visible wavelength disposed in a first marker area; and a second fluorescent pigment emitting light of the second, invisible wavelength disposed in a second marker area different from the first marker area;
wherein the luminescent pigments include a first luminescent pigment emitting light of the first, visible wavelength disposed in the first marker area; and a second luminescent pigment emitting light of the second, invisible wavelength disposed in the second marker area different from the first marker area; and
wherein the plurality of windows includes:
a first window defined in the carrier layer and disposed inside the first marker area and configured to transmit light of the first, visible wavelength; and
a second window defined in the carrier layer and disposed inside the second marker area and configured to transmit light of the second, invisible wavelength.

2. The marker according to claim 1, wherein the fluorescent pigments convert light from a light source displaced from the marker of the second wavelength to the first wavelength; and
wherein a portion of the carrier layer adjacent to the fluorescent pigment is configured to pass the second wavelength light to the fluorescent pigment and block light of the first wavelength.

3. The marker according to claim 1, wherein a portion of the carrier layer is configured to define a reference area with a predefined reflection characteristic.

4. The marker according to claim 1, further comprising a graphical pattern carried by the carrier layer.

5. The marker according to claim 1, wherein
the carrier layer provides mechanical stability;
the at least one of fluorescent pigments or luminescent pigments are disposed in a light emission layer on one face of the carrier;
the attachment layer includes an adhesive layer on the one face of the carrier and configured to attach the marker to the subject.

6. The marker according to claim 1, wherein one of the first and second wavelengths is red and the other is infrared.

7. A system for determining vital sign information of a subject comprising:
the marker according to claim 1;
an optical detector configured to detect the first and second wavelength light which passes through the first and second windows; and
a computer processor configured to determine a blood oxygen concentration of the subject from the detected light.

8. The marker according to claim 1, wherein the second fluorescent or luminescent pigment is configured to emit the light of the second wavelength toward skin of subject, wherein light of the second wavelength reflected from within the skin passes through second window of the plurality of windows.

9. The marker according to claim 1, wherein the first fluorescent or luminescent pigment is configured to emit the light of the first wavelength toward skin of the subject, wherein light of the first wavelength reflected from within the skin passes through the first window of the plurality of windows.

10. The marker according to claim 9, wherein the reflected light is encoded with information about blood in the skin.

11. A system for determining vital sign information of a subject comprising
a marker according to claim 1;
a detector physically displaced from the marker and configured to detect reflected light which passes through the at least one window of the plurality of windows; and
a computer processor configured to determine heart rate information of the subject from the detected light.

12. The system according to claim 11, wherein the detector includes a video camera.

13. A photo-plethysmographic method comprising:
emitting red light from a first fluorescent or luminescent pigment in a first marker area towards skin of a subject;
emitting infrared light from a second fluorescent or luminescent pigment in a second marker area towards skin of the subject; passing the red light and the infrared light through a plurality of windows, wherein the plurality of windows includes: a first window defined in a carrier layer and disposed inside the first marker area and configured to transmit the red light; and a second window defined in carrier layer and disposed inside the first marker area and configured to transmit the infrared light,
detecting the infrared light and the red light reflected by the skin of the subject with an optical detector displaced from the subject; and
with a computer processor, processing the detected infrared light and the detected red light to determine vital sign information of the subject.

14. The method according to claim 13, wherein an intensity of the reflected light varies in accordance with heart rate and wherein the determined vital sign includes heart rate;
the first fluorescent or luminescent pigment is configured to receive light from a light source which is displaced from the first fluorescent or luminescent pigment; and
the second fluorescent or luminescent pigments is configured to receive light from the light source which is displaced from the second fluorescent or luminescent pigment.

15. The method according to claim 13, further including:
with the computer processor, analyzing the detected infrared light and the detected red light to determine a blood oxygen concentration (SpO2).

16. The method according to claim 15, further including:
with the computer processor, processing the reflected infrared light to further determine a heart rate of the subject.

17. An apparatus for determining information indicative of a heart rate of a subject, the system comprising:
at least one marker adapted for attachment to a portion of the subject, the at least one marker including:
a carrier layer;

at least one of fluorescent pigments or luminescent pigments carried by the carrier layer;

a plurality of windows defined in the carrier layer adjacent to the at least one of fluorescent pigments or luminescent pigments and configured to pass light of a first, visible wavelength and pass light of a second, invisible wavelength;

an attachment layer disposed on the carrier layer and configured to attach the carrier layer to the subject, wherein the fluorescent pigments includes a first fluorescent pigment emitting light of the first, visible wavelength disposed in the first marker area; and a second fluorescent pigment emitting light of the second, visible wavelength disposed in a second marker area different from the first marker area;

wherein the luminescent pigments includes a first luminescent pigment emitting light of the first, visible wavelength disposed in a first member area; and a second luminescent pigment emitting light of the second, invisible wavelength disposed in the second marker area different from the first marker area; and wherein the plurality of windows includes:

a first window defined in the carrier layer and disposed inside the first marker area and configured to transmit light of the first, visible wavelength; and a second window defined in the carrier layer and disposed inside the second marker area and configured to transmit light of the second, invisible wavelength;

a camera disposed displaced from the subject and configured to detect light reflected by the skin of the subject; and a computer processor programmed to determine information indicative of a heart rate of the subject based on a time-variant intensity of the reflected light.

18. The apparatus according to claim 17, wherein the first fluorescent or luminescent pigment is configured to emit light of the first wavelength from light emitted from a light source that is displaced from the at least one marker;

wherein the second fluorescent or luminescent pigment is configured to emit light of the second wavelength from light emitted from the light source that is displaced from the at least one marker;

wherein the processor is programmed to determine a blood oxygen concentration based on the detected light of the first and second wavelengths.

19. The apparatus according to claim 17, wherein the first fluorescent or luminescent pigment is configured to emit the light of the second wavelength toward skin of subject, wherein the light of the second wavelength reflected from within the skin passes through second window of the plurality of windows.

* * * * *